United States Patent [19]

Huebner et al.

[11] Patent Number: 4,816,621
[45] Date of Patent: Mar. 28, 1989

[54] CERAMIC-METAL FEEDTHROUGH LEAD ASSEMBLY AND METHOD FOR MAKING SAME

[75] Inventors: Rosa M. Huebner, Grafing, Fed. Rep. of Germany; Ursula Huebner, Paris, France; Klaus G. Huebner, Grafing, Fed. Rep. of Germany

[73] Assignee: Siemens Aktiengesellschaft, Berlin and Munich, Fed. Rep. of Germany

[21] Appl. No.: 125,475

[22] Filed: Nov. 25, 1987

[30] Foreign Application Priority Data

Nov. 28, 1986 [DE] Fed. Rep. of Germany ....... 3640639

[51] Int. Cl.⁴ .................. H01B 17/30; C03C 27/04; B23K 1/04; B23K 1/20
[52] U.S. Cl. .................. 174/152 GM; 29/631; 228/124; 228/168; 228/249; 228/258; 403/272
[58] Field of Search ............. 174/50.56, 50.58, 50.61, 174/50.63, 152 GM; 29/631; 65/59.1, 59.3, 59.34, 59.4; 228/120, 121 R, 121 M, 122 R, 122 M, 124 R, 124 M, 168, 246, 249, 258; 403/28, 29, 30, 179, 272

[56] References Cited

U.S. PATENT DOCUMENTS 3,134,230 5/1964 Lynch .................. 174/152 GM X
3,302,961 2/1967 Franklin .................. 228/124 R X
4,225,262 9/1980 Koop et al. .................. 403/272

FOREIGN PATENT DOCUMENTS 0005312 11/1979 European Pat. Off. .... 174/152 GM
1049178 8/1953 France ................. 174/152 GM
WO80/01620 8/1980 World Int. Prop. O. ... 174/152 GM

*Primary Examiner*—Laramie E. Askin
*Attorney, Agent, or Firm*—Hill, Van Santen, Steadman & Simpson

[57] ABSTRACT

A ceramic-metal lead assembly, of the type suitable for use in nerve or heart pacemakers, has a disk of high-purity ceramic with at least one lead extending therethrough, the disk being soldered vacuum-tight to a flange ring via a solder gap. The flange ring consists of a metal which is resistant to body electrolytes, and the coefficients of thermal expansion of the joined materials are matched to each other, but are not identical. For avoiding cracks in the ceramic disk in the region of the solder connection, the solder gap has a width such that the diffusion path of the metal of the flange ring into the solder connection cannot exceed a selected distance in the solder bridge which forms at the soldering temperature. A solder zone which is free of the metal of the flange ring, and thus has a dutility which is not degraded by the flange ring metal, is formed around the ceramic disk.

15 Claims, 1 Drawing Sheet

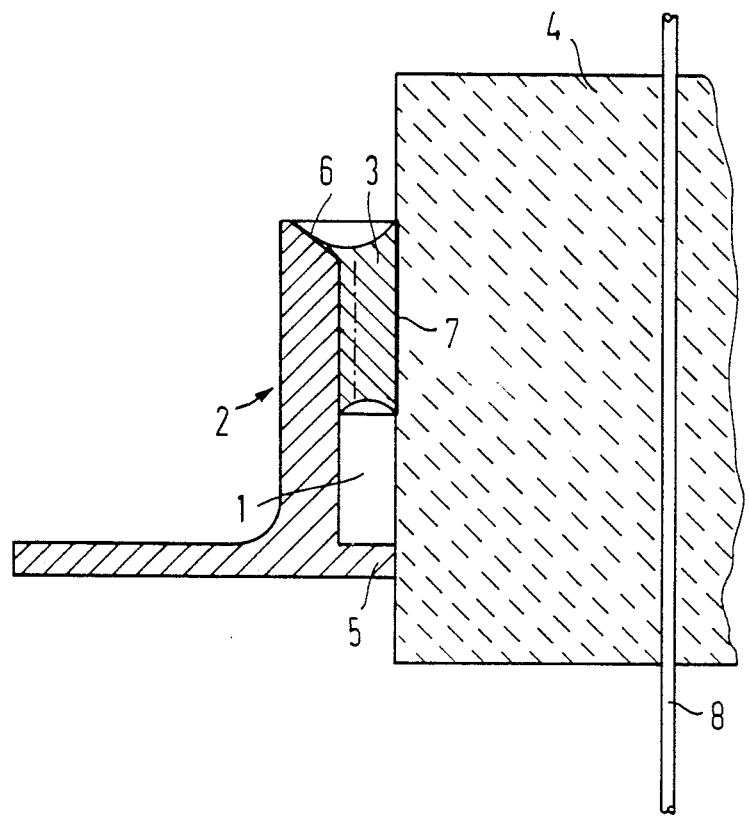

CERAMIC-METAL FEEDTHROUGH LEAD ASSEMBLY AND METHOD FOR MAKING SAME

BACKGROUND OF THE INVENTION

1. Field of the Invention

The present invention is directed to a ceramic-metal feedthrough lead assembly, and to a method for manufacturing such an assembly, and in particular to an assembly and method suitable for nerve or heart pacemakers.

2. Description of the Prior Art

Nerve or heart pacemakers are composed of essentially four components: an electronic circuit for generating the stimulation pulses and for processing control signals, a battery as the energy source, a hermetically tight encapsulation which protects the circuit and the energy source against body electrolytes, and electrodes consisting of a fatigue-resistant lead electrically insulated from the body, and terminating in an electrode head which produces the connection between the stimulation conductor (or conductors) within the lead and body tissue.

In the manufacture of such devices suitable for implantation in a patient, care must be exercised particularly in the manufacture of the ceramic feedthrough lead assembly for connecting the electrodes to the encapsulation or housing. Ceramic materials must be used which are resistant to body electrolytes, and which achieve a vacuum-tight, and thus moisture impermeable, connection. A potential loss of tightness is a particular disadvantage in such feedthrough lead assemblies, such a loss of tightness occurring as a result of crack formation in the ceramic which occurs in the vacuum-tight soldering of the metal and ceramic parts.

All previously known designs of ceramic-metal feedthrough lead assemblies are based on the assumption that the joined pieces must be very closely matched to each other in design and in their coefficients of expansion in order to resist crack formation during soldering. For this reason, conventional feedthrough lead assemblies exhibit very small gaps at the solder locations, these gaps being relatively easy to fill with solder. When soldering a titanium flange and a ceramic pearl with gold, however, titanium diffuses into the gold and vice versa. The resulting solder connection is thus extremely brittle and hard. Because the expansion of the titanium at the solder melting point is somewhat greater than that of the ceramic, the titanium contracts more than the ceramic during cooling. As a consequence, a pulling force is exerted on the ceramic, which leads to the formation of cracks in the ceramic because its tensile strength is relatively low. An interception of these tensile forces, however, is no longer possible at what is now a brittle solder connection.

SUMMARY OF THE INVENTION

It is an object of the present invention to provide a ceramic-metal feedthrough lead assembly wherein cracks in the ceramic are avoided so that the lead assembly is hermetically tight, and in particular to provide such a lead assembly suitable for devices which are intended for implantation in the human body.

It is a further object of the present invention to provide a method for manufacturing such a lead assembly.

The above objects are achieved in accordance with the principles of the present invention in a lead assembly having a disk of high purity ceramic with at least one electrode lead extending therethrough. The ceramic disk is soldered vacuum-tight to a flange ring with a solder gap being maintained between the ceramic disk and the flange ring. The flange ring consists of a metal which is resistant to body electrolytes, such as titanium or tantalum. The respective coefficients of thermal expansion of the disk and the flange are adapted, but not necessarily matched, to each other. The solder gap has a width such that the diffusion path of the metal of the flange ring into the solder connection cannot exceed a selected distance at the soldering temperature. Thus a solder zone which is free of metal of the flange ring arises. The ductility of this solder zone is thus not degraded by contamination by the metal of the flange ring. Since this solder zone is disposed at a portion of the solder connection close to and in contact with the ceramic disk, forces which would otherwise cause cracks in the ceramic can be intercepted or absorbed due to the ductility of the solder connection, thereby preserving the ceramic.

The high purity ceramic is preferably composed of aluminum oxide, or at least has an aluminum oxide proportion greater than 90%. The solder is preferably gold solder.

The width of the solder gap preferably is in the range of from about 1% through about 3% of the diameter of the ceramic disk, and a preferred gap is approximately 0.06 mm.

DESCRIPTION OF THE DRAWINGS

The single drawing is a side sectional view of a ceramic-metal feedthrough lead assembly constructed in accordance with the principles of the present invention.

DESCRIPTION OF THE PREFERRED EMBODIMENTS

As shown in the drawing, the lead assembly includes a disk 4 consisting of high purity ceramic which is soldered to a flange ring 2 consisting of a metal which is resistant to body electrolytes, such as tantalum or titanium. The soldering is undertaken vacuum-tight at a solder gap 1. The solder gap 1 has a width such that the diffision path of the metal of the flange ring 2 into the forming solder bridge or connection 3 cannot exceed a selected distance at the soldering temperature, i.e., at the melting temperature of the solder. The solder may be, for example, gold solder. The approximate termination of the diffusion distance in the solder connection 3 is indicated by a dot-dash line.

The region between the dot-dash line and the metallization 7, provided on the ceramic disk 4 for better adhesion of the solder connection 3, is free of the metal of the flange ring 2, and consists of substantially untainted solder, such as substantially untainted gold.

In the embodiment of the drawing, the flange ring 2 has an inward projection 5 which automatically defines the width of the solder gap 1. The solder connection 3 terminates above the projection 5 in the region of the metallization 7, so that no tensile forces caused by the solder connection 3 can occur in the region of the projection 5. For easier introduction of the solder into the solder gap 1, it is preferable to provide the outside end (flange collar) of the flange ring 2 with an inwardly proceeding bevel 6.

Only one electrode line 8 is shown feeding through the ceramic disk 4 in a vacuum-tight fashion in this embodiment. It will be understood by those skilled in the art, however, that a plurality of such electrode lines spaced from each other may be conducted through the ceramic disk 4. The electrode lines are preferably comprised of platinum or niobium.

A method for manufacturing the above assembly is as follows. The ceramic disk 4 is provided with the metallization layer 7 in the intended solder region. The metallization layer 7 preferably consists of titanium hydride. The ceramic disk 4 is dimensioned so that when inserted into the flange ring 2, a relatively broad solder gap 1 is formed between the disk 4 and the flange ring 2. Solder wire, such as gold wire, is then put in place on the flange collar, and the arrangement is heated in a vacuum to the melting temperature of the solder. The holding time at this temperature is maintained relatively short, preferably one minute through one and a half minutes, so that a through-diffusion or through-alloying of the metal (tantalum or titanium) of the flange ring 2 does not have time to occur through the full width of the relatively broad solder connection (solder bridge). Thus a zone of pure solder (pure gold) is obtained at the side of the connection 3 closer to the ceramic disk 4. In order to reliably accomplish soldering in this manner, it is necessary to make use of centering solder gauges or a self-centering flange, as described above.

The advantages achieved with the above lead assembly and method are that, contrary to conventional theories, the widening of the solder gap 1 between the flange ring 2 and the ceramic disk 4 (and thus "deteriorating" the geometric adaptation of the components to be soldered) avoids, rather than promotes, the formation of incipient cracks, and thus maintains the tightness of the ceramic. The widening of the solder gap in the assembly and method disclosed herein is counteracted by maintaining the holding time of the temperature at the melting point of the solder very brief during the soldering, so that a through diffusion of the relatively wide solder bridge is not possible. A zone of pure solder (pure gold) thus remains in the solder connection, and a certain ductility of the solder connection is retained. The tensile forces occurring in this assembly are thus intercepted or accommodated in this zone, and those forces do not exert a "pull" on the ceramic.

What is claimed is:

1. A feedthrough lead assembly comprising:
    a ceramic component consisting of high purity ceramic material having at least one electrode conducted therethrough, said ceramic component having a surface;
    a flange ring consisting of metal diffusible into solder, said flange ring having a surface spaced from said surface of said ceramic component forming a gap between said surfaces; and
    a solder connection bridging said gap, said gap having a width such that the diffusion path of the metal of said flange ring into said solder connection is substantially less than the width of said gap, said solder connection having a zone free of said metal of said flange ring.

2. A lead assembly as claimed in claim 1, wherein said ceramic component consists of aluminum oxide.

3. A lead assembly as claimed in claim 1, wherein said solder connection consists of gold solder.

4. A lead assembly as claimed in claim 1, wherein said flange ring has a projection extending from said surface of said flange ring to said surface of said ceramic component, said projection defining said width of said gap, and said solder connection terminating above said projection.

5. A lead assembly as claimed in claim 1, wherein said ceramic component is a disk.

6. A lead assembly as claimed in claim 5, wherein said gap has a width in the range of from about 1% through about 3% of the diameter of said ceramic disk.

7. A lead assembly as claimed in claim 1, further comprising a metallization layer on said surface of said ceramic component in registry with said solder connection.

8. A lead assembly as claimed in claim 1, wherein said flange ring has a further surface contiguous with said surface at the location of said solder connection, and wherein said further surface is beveled.

9. A lead assembly as claimed in claim 1, wherein said flange ring consists of a metal selected from the group consisting of titanium and tantalum.

10. A feedthrough lead assembly comprising:
    a disk of ceramic material having a lead conducted therethrough and having a surface;
    a metallization layer disposed on a portion of said surface of said ceramic disk;
    a flange ring consisting of metal diffusible into solder and having a projection abutting said surface of said ceramic disk, said flange ring having a surface extending parallel to said surface of said ceramic disk and spaced therefrom at a distance defined by said projection thereby forming a gap between said surfaces; and
    a solder connection bridging said gap between said surfaces, said gap having a width such that a diffusion path of the metal of said flange ring into said solder connection is substantially less than the width of said gap, said solder connection having a zone of pure solder between a termination of said diffusion path within said solder connection and said metallization layer on said surface of said ceramic disk.

11. A lead assembly as claimed in claim 10, wherein said solder consists of gold.

12. A lead assembly as claimed in claim 10, wherein said ceramic disk consists of aluminum oxide.

13. A lead assembly as claimed in claim 10, wherein said flange ring consists of a metal selected from the group consisting of tantalum and titanium.

14. A method for manufacturing a feedthrough lead assembly comprising the steps of:
    conducting a lead through a ceramic component, said ceramic component having a surface;
    spacing a surface of a flange ring consisting of metal diffusible into solder at a distance from said surface of said ceramic component;
    placing solid solder material between said surfaces of said flange ring and said ceramic component;
    heating said flange ring, said solid solder and said ceramic component in a vacuum to the melting temperature of said solder thereby forming a solder bridge between said surface of said flange ring and said surface of said ceramic component; and
    maintaining at least said solder at said melting temperature for a time period such that a diffusion path of said metal of said flange ring into said solder bridge arises which is substantially less than the distance between said surface of said flange ring and said surface of said ceramic component thereby generating a zone of pure solder in said solder bridge in contact with said ceramic component.

15. A method as claimed in claim 14 comprising the additional step of:
    metalizing at least a portion of said surface of said ceramic component at a location for contact with said solder bridge.

* * * * *